(12) United States Patent
Monod et al.

(10) Patent No.: US 6,309,868 B1
(45) Date of Patent: Oct. 30, 2001

(54) **CLONING OF THE PROLYL-DIPEPTIDYL-PEPTIDASE FROM *ASPERGILLUS ORYZAE***

(75) Inventors: Michel Monod, Lausanne; Agnes Doumas, Gollian; Michael Affolter, Pully; Peter Van Den Broek, Ch-Epalinges, all of (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/462,284

(22) PCT Filed: May 6, 1998

(86) PCT No.: PCT/EP98/02799

§ 371 Date: Mar. 24, 2000

§ 102(e) Date: Mar. 24, 2000

(87) PCT Pub. No.: WO99/02705

PCT Pub. Date: Jan. 21, 1999

(30) Foreign Application Priority Data

Jul. 5, 1997 (EP) .................................................. 97111377

(51) Int. Cl.$^7$ ............................... C12N 9/14; C12N 1/20; C12N 1/14; C12N 15/00; C07H 21/04
(52) U.S. Cl. .................. 435/195; 435/252.3; 435/254.3; 435/320.1; 435/212; 435/326; 435/254.23; 435/256.1; 435/254.11; 536/23.2; 536/23.1
(58) Field of Search ................................. 536/23.2, 23.1; 435/252.3, 320.1, 195, 254.3, 212, 254.23, 256.1, 254.11; 530/326

(56) References Cited

FOREIGN PATENT DOCUMENTS

| | | |
|---|---|---|
| 0 417 481 A | 3/1991 | (EP) . |
| 0 754 752 A2 | 1/1997 | (EP) . |
| 0 754 752 A3 | 5/1997 | (EP) . |

OTHER PUBLICATIONS

Tachi H. et al.; (1992) Phytochemistry 31: 3707–3709.
Beauvais A. et al.; (1997) Journal of Biological Chemistry 272: 6238–6244.
Heymann E. et al.; (1986) Journal of Dairy Research 53:229–236.
Beauvais A. et al.; (1997) Infection and Immunity, 65:3042–3047.
Doumas et al.; (1988) EMBL/GENBANK Databases Accession No. AJ002369.
Chemical Abstracts, Tachi, H.; (1996) Nippon Jozo Kyokaishi 91:138–140 Abstract.
Derwent Abstract for JP 07 115 969 A May, 1995.
Derwent Abstract for JP 09 000 249 A, Jan., 1997.
International Search Report for PCT/EP 98/02799.

*Primary Examiner*—Rebecca E. Prouty
*Assistant Examiner*—M. Monshipouri
(74) *Attorney, Agent, or Firm*—Winston & Strawn

(57) ABSTRACT

The invention has for object the new recombinant prolyl-dipeptidyl-peptidase enzyme (DPP IV) from *Aspergillus oryzae* comprising the amino-acid sequence from amino acid 1 to amino acid 755 of SEQ ID NO:2 or functional derivatives thereof, and providing a high level of hydrolyzing specificity towards proteins and peptides starting with X-Pro- thus liberating dipeptides of X-Pro type, wherein X is any amino acid. The invention also provides a DNA molecule encoding the enzyme according to the invention, cells expressing the enzyme according to the invention by recombinant technology, an Aspergillus naturally providing a prolyl-dipeptidyl-peptidase activity which has integrated multiple copies of the Aspergillus native promoter which naturally directs the expression of the gene encoding the prolyl-dipeptidyl-peptidase activity, Aspergillus naturally providing a prolyl-dipeptidyl-peptidase activity which is manipulated genetically so that the dppIV gene is inactivated. The invention provides a method for producing the enzyme according to the invention, comprising cultivating the cells of the invention in a suitable growth medium under conditions that the cells express the enzyme, and optionally isolating the enzyme in the form of a concentrate. The invention provides the use of the enzyme or the cells of the invention to hydrolyze protein containing materials. The invention provides the use of an enzyme and/or a cell providing a prolyl-dipeptidyl-peptidase activity, in combination with at least an enzyme providing a prolidase to hydrolyze protein containing materials. In a last further aspect, the invention provides a food product comprising a protein hydrolyzate obtainable by fermentation with at least a microorganism providing a prolyl-dipeptidyl-peptidase activity higher than 50 mU per ml when grown in a minimal medium containing 1% (w/v) of wheat gluten.

19 Claims, No Drawings

CLONING OF THE PROLYL-DIPEPTIDYL-PEPTIDASE FROM *ASPERGILLUS ORYZAE*

TECHNICAL FIELD

The present invention relates to a new recombinant prolyl-dipeptidyl-peptidase from *Aspergillus oryzae*, a gene encoding this enzyme, recombinant cells expressing this enzyme, and methods for hydrolysing protein containing materials.

BACKGROUND ART

Hydrolysed proteins, which are widely used in the food industry, may be prepared by hydrolysis of protein material with acid, alkali or enzymes. However, on the one hand, acid or alkaline hydrolysis can destroy the essential amino acids produced during hydrolysis thus reducing the nutritional value, whereas enzymatic hydrolysis rarely goes to completion so that the hydrolysed protein contains substantial amounts of peptides.

The filamentous ascomycete *Aspergillus oryzae* is known to secrete a large variety of amylases, proteinases and peptidases, the action of which are essential for the efficient solubilisation and hydrolysis of raw materials (see WO94/25580). Various methods have been used *Aspergillus oryzae* for the preparation of food products, especially methods involving the use of a koji culture.

EP417481 (Nestlé) thus describes a process for the production of a fermented soya sauce, in which a koji is prepared by mixing an *Aspergillus oryzae* koji culture with a mixture of cooked soya and roasted wheat, the koji is then hydrolysed in aqueous suspension for 3 to 8 hours at 45° C. to 60° C. with the enzymes produced during fermentation of the Aspergillus oryzae koji culture, a moromi is further prepared by adding sodium chloride to the hydrolysed koji suspension, the moromi is left to ferment and is then pressed and the liquor obtained is pasteurized and clarified.

EP429760 (Nestlé) describes a process for the production of a flavouring agent in which an aqueous suspension of a protein-rich material is prepared, the proteins are solubilized by hydrolysis of the suspension with a protease at pH6.0 to 11.0, the suspension is heat-treated at pH 4.6 to 6.5, and the suspension is ripened with enzymes of a koji culture fermented by *Aspergillus oryzae*.

Likewise, EP96201923.8 (Nestlé) describes a process for the production of a meat flavour, in which a mixture containing a vegetal proteinaceous source and a vegetale carbohydrates containing source is prepared, said mixture having initially at least 45% dry matter, the mixture is inoculated with a koji culture fermented by *Aspergillus oryzae* and by one or more another species of microorganisms involved in the traditional fermentation of meat, and the mixture is incubated until meat flavours are formed.

Depending on the nature of the protein and the enzymes used for proteolysis, the peptides formed can however have extremely bitter tastes and are thus organoleptically undesirable. There is hence a need for methods of hydrolysing proteins leading to high degree of protein hydrolysis and to hydrolysates with excellent organoleptic properties.

In addition, in protein rich materials subjected to enzymatic hydrolysis, a high level of glutaminase is required to convert glutamine into glutamic acid which is an important natural taste enhancer (see WO95/31114). Biochemical analysis of residual peptides in cereals hydrolysed by *Aspergillus oryzae*, i.e. wheat gluten, shows however that a considerable amount of glutamine remains sequestered in proline containing peptides (Adler-Nissen, In: Enzymatic hydrolysis of food proteins. Elsevier Applied Sciences Publishers LTD, p120, 1986). There is hence a need for methods of hydrolysing proteins leading to liberation of high amount of glutamine.

Among the different proteases known from koji molds, two neutral endopeptidase (Nakadai et al., Agric. Biol. Chem., 37, 2695–2708, 1973), an alkaline endopeptidase (Nakadai et al., Agric. Biol. Chem., 37, 2685–2694, 1973), an aspartic protease (Tsujita et al., Biochem. Biophys Acta, 445, 194–204, 1976), several aminopeptidases (Ozawa et al., Agric. Biol. Chem., 37, 1285–1293, 1973), several carboxypeptidases (Nakadai et al., Agric. Biol. Chem., 37, 1237–1251, 1970) have been identified and purified.

More recently a prolyl-dipeptidyl-peptidase activity has been detected in *Aspergillus oryzae*, which is an enzyme providing a high level of hydrolysing specificity towards proteins and peptides starting with X-Pro- thus liberating dipeptides of X-Pro type, wherein X is any amino-acid (Tachi et al., Phytochemistry, 31, 3707–3709, 1992).

SUMMARY OF THE INVENTION

The present invention has for object the new recombinant prolyl-dipeptidyl-peptidase (DPP IV) from *Aspergillus oryzae* comprising the amino-acid sequence from amino acid 1 to amino acid 755 of SEQ ID NO:2 or functional derivatives thereof.

In a second aspect, the invention also provides a DNA molecule encoding the enzyme according to the invention.

In a third aspect, the invention provides a cell expressing the enzyme according to the invention by recombinant technology.

In a fourth aspect, the invention provides an Aspergillus naturally providing a prolyl-dipeptidyl-peptidase activity which has integrated multiple copies of the Aspergillus native promoter which naturally directs the expression of the gene encoding the prolyl-dipeptidyl-peptidase activity.

In a fifth aspect, the invention provides an Aspergillus naturally providing a prolyl-dipeptidyl-peptidase activity which is manipulated genetically so that the dppIV gene is inactivated.

In a sixth aspect, the invention provides a method for producing the enzyme according to the invention, comprising cultivating the cells of the invention in a suitable growth medium under conditions that the cells express the enzyme, and optionally isolating the enzyme in the form of a concentrate.

In a seventh aspect, the invention provides the use of the enzyme or the cells of the invention to hydrolyse protein containing materials.

In another aspect, the invention provides the use of an enzyme and/or a cell providing a prolyl-dipeptidyl-peptidase activity, in combination with at least an enzyme providing a prolidase to hydrolyse protein containing materials.

In a last further aspect, the invention provides a food product comprising a protein hydrolysate obtainable by fermentation with at least a microorganism providing a prolyl-dipeptidyl-peptidase activity higher than 50 mU per ml when grown in a minimal medium containing 1% (w/v) of wheat gluten.

DETAILED DESCRIPTION OF THE PREFERRED EMBODIMENTS

Within the following description, the percentages are given by weight except where otherwise stated, and the amino acid or nucleotide sequences referred as "SEQ ID NO:" are always presented in the sequence listing hereafter.

Likewise, the expression "functional derivative of an enzyme" includes all amino acid sequences which differ by substitution, deletion, addition of some amino acids, for instance 1–20 amino acids, but which keep their original activities or functions. The selection of a functional derivative is considered to be obvious to one skilled in the art, since one may easily creates variants of the DPP IV (having the amino acid sequence SEQ ID NO:2) by slightly adapting methods known to one skilled in the art, for instance the methods described by Adams et al. (EP402450; Genencor), by Dunn et al. (Protein Engineering, 2, 283–291, 1988), by Greener et al. (Strategies, 7, 32–34, 1994), and/or by Deng et al. (Anal. Biochem, 200, 81, 1992).

In particular, a protein may be generally considered as a derivative to another protein, if its sequence is at least 80% identical to the protein, preferably at least 90%, in particular 95%. In the context of the present disclosure, the identity is determined by the ratio between the number of amino acids of a derivative sequence which are identical to those of the DPP IV having the amino acid sequence SEQ ID NO:2 (mature sequence 1–755), and the total number of or amino acids of the said derivative sequence.

In addition, the term "koji" designates the product of the fermentation with a koji mold culture of a mixture of a source of proteins and a source of carbohydrates, especially of a mixture of a leguminous plant or of a cooked oleagginous plant and of a cooked or roasted cereal source, for example of a mixture of soya or cooked beans and of cooked or roasted wheat or rice.

The present invention thus concerns the new prolyl-dipeptidyl-peptidase enzyme originating from *Aspergillus oryzae* which comprises the amino-acid sequence from amino acid 1 to 755 of SEQ ID NO:2 or functional derivatives thereof. This enzyme may be operably fused to a leader peptide facilitating its secretion in a host where the enzyme is expressed, for example the *Aspergillus oryzae* leader peptide having the amino-acid sequence from amino acid −16 to −1 of SEQ ID NO:2 or functional derivatives thereof.

A dppIV gene encoding the DPP IV according to the invention may at least comprise the coding parts of the nucleotide sequence SEQ ID NO:1, or functional derivatives thereof due to the degeneracy of the genetic code. This sequence is in fact interrupted by a non-coding sequence, called intron, that is spliced during in-vivo transcription (exon I at 1836–1841 bp; exon II at 1925–1924 bp; intron at 1842–1924 bp).

A dppIV gene may be obtained in substantially purified form by using the method described within the following examples from any strain of *Aspergillus oryzae*. Alternatively, a dppIV gene may be (1) detected also from other genera or species of microorganisms by use of DNA probes derived from the nucleotide sequence SEQ ID NO:1 in a stringent hybridization assay, and (2) recovered by the well known Reverse-PCR method by use of suitable primers, for example primers SEQ ID NO:8 and 9. In a further aspect, a dppIV gene may also be in-vitro synthesized and then multiplied by using the polymerase chain reaction, for instance.

The DNA molecule according to the invention at least comprises a dppIV gene encoding the DPP IV of the invention. This molecule may be in a form of a vector, i.e. a replicative plasmid or an integrative circular or linearized non replicative plasmid. The DNA molecule thus may comprise, operably linked to the dppIV gene, regulatory sequences native to the organism from which derives the gene. Said native regulatory sequences may be the promoter, the terminator, and/or a DNA sequence encoding a signal sequence that originally regulated the secretion of the dppIV gene, such as the *Aspergillus orzyzae* nucleotide sequence coding for a signal peptide from nucleotide 1836 to nucleotide 1966 of SEQ ID NO:1 (without the intron) or functional derivatives thereof due to the degeneracy of the genetic code. In another embodiment, regulatory sequences may be native sequences that regulate a different gene in the said organism of origin or that regulate a different gene in a foreign organism, for example. A regulatory sequence other than the native regulatory sequence will generally be selected for its high efficiency or desirable characteristic, for example inducibility of a promoter or a sequence encoding a peptide signal which will permit secretion of the protein.

If heterologous expression is preferred, meaning that the genes of the invention are expressed in another organism than the original host (strain, variety, species, genus, family, order, class or division) the regulatory sequences are preferably derived from an organism similar or equal to the expression host. For example, if the expression host is a yeast cell, then the regulatory sequences will be derived from a yeast cell. The promoter suitable for constitutive expression, preferably in a fungal host, may be a promoter from the following genes: glycerolaldhehyde-3-phosphate dehydrogenase, phospho-glycerate kinase, triose phosphate isomerase and acetamidase, for example. Promoter suitable for inducible expression, preferably in a fungal host, may be a promoter from the following genes: endoxylanase IIA, glucoamylase A, cellobiosehydrolase, amylase, invertase, alcohol dehydrogenase and amyloglucosidase. The selection of a desirable regulatory sequence operably linked to a sequence of the invention and capable of directing the expression of the said nucleotide sequence is considered to be obvious to one skilled in the art.

The DNA molecule according to the invention may also comprise a selection marker to discriminate host cells into which the recombinant DNA material has been introduced from cells that do not comprise the said recombinant material. Such marker genes are, for example in case fungal expression is preferred, the known ga-2, pyrG, pyr4, pyrA, trpC, amdS or argB genes. The DNA molecule may also comprise at least one suitable replication origin. Suitable transformation methods and suitable expression vectors provided with a suitable transcription promoter, suitable transcription termination signals and suitable marker genes for selecting transformed cells are already known in the literature for many organisms including different bacteria, fungal and plant species. In the event fungal expression is required, the expression system described in EP278355 (Novartis) may be thus particularly adapted.

Recombinant koji molds may be obtained by any method enabling a foreign DNA to be introduced into a cell. Such methods include transformation, electroporation, or any other technique known to those skilled in the art.

The invention thus encompasses a recombinant cell comprising the DNA molecule of the invention, the said cell being able to express the DPP IV of the invention or functional derivatives thereof. These cells may be derived from the group of fungal, yeast, bacterial and plant cells. Preferably, yeast cells are of the genera Saccharomyces, Kluyveromyces, Hansenula and Pichia, bacterial cells are Gram negative or positive bacteria, i.e. of the genera Escherichia, Bacillus, Lactobacillus, Lactococcus, Streptococcus and Staphylococcus, plant cells are of the vegetable group, and fungal cells are cells that are traditionally used for making a koji, such as Aspergillus, Rhizopus and/or Mucor species, notably *Aspergillus soyae, Aspergillus oryzae* (ATCC 20386), *Aspergillus phoenicis* (ATCC 14332), *Aspergillus niger* (ATCC 1004), *Aspergillus awamori* (ATCC 14331), *Rhizopus oryzae* (ATCC 4858), *Rhizopus oligosporus* (ATCC 22959), *Rhizopus japonicus* (ATCC 8466), *Rhizopus formosaensis, Mucor circinelloides* (ATCC 15242), *Mucor japanicus, Penicillium glaucum* and *Penicillium fuscum* (ATCC 10447). Strains referred by an ATCC number are accessible at the American Type Culture Collection, Rockville, Md. 20852, US. The invention is not limited by such indications which were rather give to enable one skilled in the art to carry out the invention.

Recombinant cells of the invention may comprise the DNA molecule of the invention stably integrated into the chromosome or on a replicative plasmid. Among all recombinant cells of the invention thus created, the present invention has particularly for object the strains *A. oryzae* CNCM I-1887, *A. oryzae* CNCM I-1888 and *Pichia pastoris* CNCM I-1886.

Preferably, functional copies of the dppIV gene are integrated at a predefined locus of the chromosomal DNA of the host cell.

Accordingly, in order to operably integrate into the chromosome of prokaryotic cells at least one functional dppIV gene which is not fused to any promoter, the DNA molecule of the invention may be integrated by using the process described in EP564966, i.e., (1) transforming a host strain organism with a donor plasmid which does not replicate in the host strain, wherein the donor plasmid comprises a vector backbone and a dppIV gene of the invention operably integrated, without any promoter, into a part of an operon of the host strain, maintaining the frame and the function of the genomic operon of the host strain; (2) identifying cointegrate transformants in which the complete donor plasmid is integrated into the genomic operon of the host strain; and (3) selecting an integrant transformant from the cointegrate transformants, wherein the genome of the selected integrant transformant does not include the vector backbone of the donor plasmid but does include the dppIV gene, which is operably integrated into the conserved genomic operon and which is stably maintained and expressed due to selective pressure on the correct functioning of the essential cistron upon growth in a standard medium.

In a second embodiment, in order to stably integrate into the chromosome of eucaryotic cells only one functional dppIV sequence which is fused to a promoter and a terminator which are native to the host organism, DNA molecule of the invention may be integrated by slightly adapting the process of de Ruiter-Jacobs, Y.M.J.T., Broekhuijsen et al. (A gene transfer system based on the homologous pyrG gene and efficient expression of bacterial genes in *Aspergillus oryzae. Curr. Genet.* 16: 159–163, 1989), i.e., (1) preparing a non-replicative DNA fragment by ligating the dppIV, which is operably linked to a promoter and terminator that are native to the host organism, downstream a DNA sequence encoding any essential gene, said essential gene being inactivated by at least a mutation and/or a deletion (this essential gene may be a gene involved in uracil biosynthesis, such as the pyrG gene in case *A. oryzae* is used, for example); (2) selecting a host organism containing the essential gene which is however inactivated by another mutation(s) or deletion(s); (3) transforming said host organism with the non-replicative DNA fragment; (4) identifying integrate transformants in which the DNA fragment is integrated so as to restaure the native function of the essential gene; (5) selecting an integrate transformant in which only one DNA fragment is integrated.

Progeny of an expression host comprising a DNA molecule according to the invention is also included in the present invention. Accordingly, a preferred embodiment of the invention is directed to a cell comprising a recombinant DNA molecule of the invention in any of the embodiments described above, wherein the said cell is able to integrate the DPP IV into the cell wall or the cell membrane or secrete the enzymes into the periplasmic space or into the culture medium. The secreting route to be followed by the recombinant protein according to the invention will depend on the selected host cell and the composition of the recombinant DNA according to the invention. Most preferably, however, the protein will be secreted into the culture medium. To this end, the cell according to the invention may comprise a recombinant dppIV gene further operably linked to a DNA encoding a foreign leader sequence (pre or prepro), for example.

Cells over-expressing the DPP IV of the invention are preferably chosen, especially Aspergillus cells capable of providing at least 50 mU, especially at least 100 mU, of DPP IV activity per ml of supernatant when grown in a minimal medium containing 1% (w/v) of wheat gluten, such as the MMWG medium.

These cells may be obtained by incorporation of the DNA molecule of the present invention in an expression host, said DNA molecule comprising one or more regulatory sequences which serve to increase expression levels of the protein(s) of the invention.

The over-expression can be further achieved by introducing multicopies of the DNA molecule of the invention, for example. Surprisingly, Aspergillus cells having integrated multiple recombinant functional dppIV genes of the invention may provide a DPP IV activity per ml of supernatant which is more than it should have been compared to the number of integrated copies, probably due to the titration of a negatively acting transcription factor. As an example, the *Aspergillus oryzae* transformant 6 of the following example 1 was deposited under the Budapest Treaty at the CNCM where it receives the deposit number CNCM I-1888.

In addition, it has also been shown that over-expression of the DPP IV may be achieved in Aspergillus species naturally providing a prolyl-dipeptidyl-peptidase activity, by integrating multiple copies of the Aspergillus native promoter which naturally directs the expression of the gene encoding the prolyl-dipeptidyl-peptidase activity. The promoter region of *Aspergillus oryzae* contained in the nucleotide sequence from nucleotide 1 to nucleotide 1835 of SEQ ID NO:1 is of particular interest for this purpose. As an example, the *Aspergillus oryzae* transformant B2 of the following example 4 was deposited under the Budapest Treaty at the CNCM where it receives the deposit number CNCM I-1887.

The invention is also directed to a process for producing the DPP IV of the invention comprising, providing recombinant cells according to the invention in a suitable growth medium under conditions that the cells express the DPP IV, and optionally isolating the said recombinant protein(s) in the form of a concentrate. The selection of the appropriate medium may be based on the choice of expression host and/or based on the regulatory requirements of the DNA recombinant material. Such media are well-known to those skilled in the art.

After fermentation, the cells can be removed from the fermentation broth by centrifugation or filtration. Depending on whether the host cells have secreted the DPP IV of the invention into the medium or whether the DPP IV are still connected to the host cells in some way either in the cytoplasm, in the periplasmic space or attached to or in the membrane or cell wall, the cells can undergo further treatment to obtain the recombinant protein. In the latter case, where the recombinant enzyme is still connected to the cells, recovery may be accomplished by rupturing the cells for example by high pressure, sonication, enzymatic digestion or simply by cell autolysis followed by subsequent isolation of the desired product. The DPP IV can be separated from the cell mass by various methods, such as ultrafiltration, and then subsequently precipitated with an organic solvent. The isolated DPP IV may be further purified by conventional methods such as precipitation and/or chromatography.

The present invention also relates to the use of the purified DPP IV or the above mentioned cells to hydrolyse protein containing materials, such as mixtures of a source of proteins and a source of carbohydrates, especially of a mixture of a leguminous plant or of a cooked oleaginous plant and of a cooked or roasted cereal source, for example of a mixture of soya or cooked beans and of cooked or roasted wheat or rice. Compositions containing wheat gluten are particularly adapted for the purpose of the present invention, since considerable amount of glutamine remains sequestered in proline containing peptides when wheat gluten is hydrolysed by traditional koji cultures.

To obtain a satisfactory degree of hydrolysis, the purified DPP IV may suitably be added to the proteinaceous material in a amount of 0.05–15 Unit/ 100 g of protein, in particular 0.1–8 Unit/100 g of protein. The incubation may be performed at a pH from between about 4 and about 10, preferably between about 5 and about 9. The incubation may be performed at any convenient temperature at which the enzyme preparation does not become inactivated, i.e. in the range of from about 20° C. to about 70° C.

In addition, in the event one may try, after or during hydrolysis with DPP IV, to further liberate as much as possible glutamine linked to proline residues, the present invention provides a method in which the DPP IV of the invention is used in combination with at least an enzyme providing a prolidase activity that is to say an enzyme which has a high level of specificity towards dipeptides of the X-Pro type (Ezespla et al., Ap. Env. Microb., 63, 314–316, 1997; Such kind of enzyme is already available from Sigma: E.C. 3.4.13.9).

In a further aspect, the present invention relates to a food product comprising a protein hydrolysate obtainable by fermentation with at least a microorganism providing a prolyl-dipeptidyl-peptidase activity higher than 50 mU per ml when grown in a minimal medium containing 1% (w/v) of wheat gluten.

Important food products of the present invention is an ingredient of a mother milk substitute for infants, or a hydrolysed vegetable protein ingredient, i.e. a koji. Indeed, if the DPP IV activity (enzyme or microorganism) is combined with other proteolytic activities (enzymes or microorganisms), i.e. typically if *Pichia pastoris* CNCM I-1886 or *Aspergillus oryzae* CNCM I-1887 or CNCM I-1888 or enzyme purificates thereof are used, high degree of hydrolysis may be obtained leading to a non-bitter flavour and a significantly lower allergenicity than unhydrolysed proteins. The milk substitute may be further formulated in substantially the same way as that indicated in the prior literature for products of this type (cf. EP 96202475.8).

The present invention is not to be limited in scope by the specific embodiments described herein. Indeed, various modifications of the invention, in addition to those described herein, will become apparent to those skilled in the art from the foregoing description and accompanying figures. Such modifications are intended to fall within the scope of the claims. Various publications are cited herein, the disclosures of which are incorporated by reference in their entireties to the extent necessary for understanding the present invention. DNA manipulation, cloning and transformation of bacteria cells are, except where otherwise stated, carried out according to the textbook of Sambrook et al. (Sambrook et al., Molecular Cloning, A Laboratory Manual, Cold Spring Harbor Laboratory Press, U.S.A., 1989). These examples are preceded by a brief description of the plasmids and strains used, and by the composition of various media. The strains *A. oryzae* TK3, *A. oryzae* transformant 6 (example 1), *A. oryzae* transformant B2 (example 4), *Pichia pastoris* containing pKJ 115 (example 3) were deposited under the Budapest Treaty, at the Collection Nationale de Culture de Microorganismes (CNCM), 25 rue du docteur Roux, 75724 Paris, France, on Jun. 24, 1997, where they receive respectively the deposit numbers CNCM I-1882, CNCM I-1888, CNCM I-1887 and CNCM I-1886. All restrictions as to the availability of these deposits will be withdrawn upon first publication of this application or another application which claims benefit of priority to this application.

Strains and Plasmids

*Aspergillus oryzae* 44 and TK3 originate from the Nestlé strain collection. However other wild type *Aspergillus oryzae* strains may also have been used in the context of the following examples.

*A. oryzae* NF1 derived from TK3 by targeted disruption (uridine auxotrophe).

*Aspergillus nidulans* 033 (biA 1, argA1) can be obtained through Fungal Genetic Stock Center, Glasgow, and is used as a source of pyrG (GenBank accession number M19132) gene. However other wild type *Aspergillus nidulans* strains may also have been used in the context of the following examples.

The *Pichia pastoris* (Invitrogen Inc., US)

Plasmid pMTL21-H4.6 containing the *Aspergillus fumigatus* dppIV gene can be provided by the Institut Pasteur, Paris, France (Beauvais et al., An homolog of the CD26 is secreted by the human pathogenic fungus *Aspergillus fumigatus*, Infect. immun. In press., 1997; GenBank EMBL, accession number: V87950).

Plasmid pNFF28 contains the *A. oryzae* TK3 pyrG gene (GenBank EBI/UK, accession number: Y13811).

Plasmids pMTL20 (Chambers et al., Gene, 68, 139–149, 1988; GenBank EMBL, accession number: M21875), pNEB 193 (Biolabs, New England) and pBluescriptSK⁻ (Stratagene, US) were used in subcloning procedures.

Plasmid pCL1920b is a derivative of plasmid pCL1920 (Lerner and Inouye, Nucleic Acids Research, 18, 4631, 1990) in which the multiple cloning site was modified to include a SmaI site and a EcoRI site between the BamHI and SalI sites.

The *P. pastoris* expression vector pKJ115 was constructed by cloning the expression cassette of pPIC9 (Invitrogen) in pCL1920b. In pKJ115 the expression cassette of pPIC9 is flanked by two SmaI sites for linearisation of the DNA, before transformation of *P. pastoris*.

Growth Media

*Aspergillus oryzae* can grow on the minimal medium (MM) prepared according to Pontecorvo et al. (Adv. Genet., 5, 141–239, 1953).

*Aspergillus oryzae* NF1 is grown at 35° C. on MM containing 10 mM NaNO$_3$ as a nitrogen source and 10 mM uridine.

MMWG contains MM plus 1% (w/v) of wheat gluten (WG) (Sigma),

MMWGH contains MM and 0.1% (w/v) WG (Sigma) plus 0.1% (w/v) WG hydrolysate prepared hydrolysing non-vital wheat gluten powder (Roquette, France) with Alcalase 2.4 L (Novo Nordisk, Denmark). Hydrolysis is conducted at 20% (w/w) substrate concentration and an enzyme to substrate ratio (E/S) of 1:50 (by weight of protein) for 6 h at 60° C. and constant pH of 7.5 (pH stat). Alcalase is then heat inactivated at 90° C. for 10 min. After centrifugation of the hydrolysate, the supernatant is lyophilised to give WGH and stored at room temperature. WGH contains mainly peptides and only minimal amounts of free amino acids. Peptide mass distribution in WGH is from 200 to 10'000 Da, determined by size-exclusion chromatography on a Superdex Peptide column.

*P. pastoris* can grow on RDB (Regeneration Dextrose Base): 1M sorbitol, 1% (w/v) dextrose, 1.34% (w/v) yeast nitrogen base (YNB), $4 \times 10^{-5}$% (w/v) biotine, $5 \times 10^{-3}$% aa (i.e. $5 \times 10^{-3}$% (w/v) of each L-glutamic acid, L-methionine, L-lysine, L-leucine and L-isoleucine.

MMM (Minimal Methanol Medium): 1.34% (w/v) YNB, $4 \times 10^{-5}$% (w/v) biotine, 0.5% (w/v) methanol.

BMGY (Buffered minimal Glycerol-complex Medium): 1% (w/v) yeast extract, 2% (w/v) peptone, 10 mM potassium phosphate pH 6.0, 1.34% (w/v) YNB, $4 \times 10^{-5}$% (w/v) biotine, 1% (w/v) glycerol.

BMMY: (Buffered minimal Methanol-complex Medium): 1% (w/v) yeast extract, 2% (w/v) peptone, 10 mM potassium phosphate pH 6.0, 1.34% YNB, $4 \times 10^{-5}$% (w/v) biotine, 0.5 (w/v) % methanol.

EXAMPLES

Example 1

Cloning of the dppIV

Screening of a genomic library: a genomic DNA library was prepared using the DNA from *A. oryzae* 44 and screened with a DNA fragment containing the dppIV gene of *Aspergillus fumigatus* (Beauvais et al., GenBank EMBL, accession number: V87950).

For this purpose, the isolation of the genomic DNA was performed according to a modified protocol of the method described by Raeder and Broda (*Let. appl. Microbiol.*, 1, 17–20, 1985). Mycelium was harvested by filtration, immediately frozen in liquid nitrogen and lyophilised. It was then grinded to a fine powder using a mortar and pestle. 200 mg of the powdered mycelium was resuspended in 2.5 ml of extraction buffer (200 mM Tris-HCl pH 8.5 150 mM NaCl, 25 mM EDTA, 0.5% SDS) and the solution was extracted with 1.75 ml extraction buffer-equilibrated phenol and 0.75 ml of chloroform/isoamylalcohol (24:1, v/v). The mixture was centrifuged (20 min, 3000 g). The aqueous phase was retrieved and incubated with 125 μl of RNAse A (Boehringer) solution (10 mg/ml) for 10 min at 37° C. 1.25 ml of 2-propanol (Merck) were then added. The pellet was washed with 70% ethanol and finally resuspended in 500 ml of TE buffer (10 mM Tris-HCl pH 8.0, 1 mM EDTA). 500 μl of 2×QBT (1.5 M NaCl, 100 mM MOPS, 30% ethanol, pH 7.0) were added to the sample which was then applied to a "Genomic-tip" (Qiagen), rinsed and eluted as recommended by the supplier.

The genomic DNA was then partially digested with Sau3A, and DNA fragments of 12–20 kb were isolated from low melting agarose (Biorad). These fragments were inserted into bacteriophages using the λ EMBL3 BamHI arm cloning system (Promega, US).

40000 recombinant plaques of the *A. oryzae* 44 genomic library in λ EMBL3 were immobilised on nylon membranes (Genescreen, Dupont). These filters were probed, with the $^{32}$P-labelled 2.3 kb dppIV insert of pMTL21-H4.6 amplified by PCR in a 5×SSC solution containing 20% formamide, 1% sodium dodecyl sulfate (SDS), and 10% dextran sulfate at 42° C. for 20 h. Labelling of DNA was performed using a random-primed DNA labelling kit (Boehringer) and ($\alpha^{32}$P)-dATP. The membranes were exposed to X-ray film after two 20 min washes in 3×SSC-1% SDS at 40° C.

Ten positive clones were isolated and purified. Restriction enzyme analysis of purified bacteriophage DNA revealed that the clones carried similar but not identical DNA fragments. By Southern analysis, the dppIV gene was assigned to an ApaI-EcoRV 4.8 kb fragment which was subcloned into pBluescriptSK⁻, creating the plasmid pNFF125.

Checking of functionalities: plasmid pNFF125 was introduced into *A. oryzae* NF1 by cotransformation with plasmid pNFF28, carrying the pyrG gene for selection of transformants.

For this purpose, *A. oryzae* NF1 was grown overnight in MM with 50 mM glucose, 5 mM glutamine and 10 mM uridine. The mycelium was harvested by sterile over cheese cloth filtration, washed once with sterile double distilled water and once with K0.8MC (20 mM MES-HCl pH 5.8, 0.8 M KCl 50 mM CaCl₂). 2 g of mycelium were resuspended in 20 ml of a filter sterilised 5 mg/ml solution of Novozyme 234 in K0.8MC. The mycelium suspension was incubated at 30° C. for 2 hours with gentle agitation (120 rpm). The protoplasts were liberated from the mycelium by gentle resuspension with a pipette, washed twice with 20 ml of S1.0TC (10 mM Tris-HCl pH 7.5, 1 M Sorbitol, 50 mM CaCl₂) and were resuspended at a final concentration of $10^8$/ml in S1.0TC. 20 ml of DNA was mixed with 200 ml of protoplasts and 50 ml of 25% PEG 6000 (BDH) in 10 mM Tris-HCl pH 7.5, 50 mM CaCl₂ and incubated for 20 min on ice. To this mixture, 2 ml of 25% PEG 6000 in 10 mM Tris-HCl pH 7.5, 50 mM CaCl₂ were added, gently mixed and incubated for 5 min at room temperature. 4 ml of S1.0TC was added and 1.0 ml aliquots were mixed with 5 ml of 2% low melting point agarose (Sigma) SMM (MM plus 50 mM glucose and 5 mM glutamine, osmotically stabilised with 1.0 M sucrose) and plated onto SMM agar (Difco).

Ninety-five pyrG⁺ transformants were screened for DPP IV activity after incubation (2 days, 30° C.) on MMWGH. For this purpose, spores of transformants were resuspended in SP2 buffer (20 mM KH₂PO₄ adjusted to pH 2.0 with HCl and 0.9% NaCl) in microtiter plates and replica plated onto Petri dishes containing MMWGH covered by a Whatman filter (Chr1). The plates were incubated for 2 days at 30° C. DPP IV activity was detected on the filter according to Lojda (Histochemistry, 54, 299–309, 1977) and Aratake et al. (Am. J. Clin. Pathol., 96, 306–310, 1991). Filters were reacted with a solution of 3 mg glycyl proline 4-β naphthylamide (Bachem) in 0.25 ml N,N-dimethylformamide (Merck) and 5 mg o-dianisidine, tetrazotized (Sigma) in 4.6 ml 0.1 M sodium phosphate buffer pH 7.2 for 10 min at room temperature. Endoproteolytic enzyme activity was also measured with resorufin-labeled casein according to Boehringer method description supplied with the substrate (Resorufin-labeled casein, Cat.No. 1080733). Leucine aminopeptidase and dipeptidyl peptidase IV activities were determined by UV spectrometry with synthetic substrates Leu-pNa and Ala-Pro-pNa (Bachem, Switzerland), respectively, according to Sarath et al. (Protease assay methods in Proteolytic enzymes: a practical approach, IRL Press, Oxford, 1989). 10 mM substrate stock solution in dimethylsulfoxide (DMSO) was diluted with 100 mM sodium phosphate buffer, pH 7.0, to a final concentration of 0.5 mM. 20–100 μl culture medium supernatant was added and reaction proceeded for up to 60 min at 37° C. A control with blank substrate and blank supernatant was done in parallel. The release of the chromophoric group 4-nitroaniline ($\epsilon$: 10'500 $M^{-1}cm^{-1}$) was measured at 400 nm and activities were expressed as mU/ml (nmol/min/ml).

Results show that sixteen transformants exhibited a clearly increased staining compared to the wild type. Seven transformants numbered 1 to 7 were selected because of their high DPP IV activity. Southern blots of them confirmed that the increase in the activity was due to the integration of multiple copies of the 4.8 kb ApaI-EcoRV fragment in the genome of the transformants. From densitometric scans of these Southern blots, it was estimated that in transformant 1, at least 4 additional copies had been functionally integrated into the genomic DNA, while, in transformant 6, they were at least 9 additional copies.

To quantify the increase of DPP IV activity in the transformants 1 and 6, these were grown in parallel with control A. oryzae NF1 pyrG+, for 7 days at 30° C. without shaking in 100 ml liquid MMWG. Analyses of the supernatants are shown in Table 1. Transformants 1 and 6 showed a DPP IV activity of at least 8 and 17 times more, respectively, than A. oryzae NF1 pyrG+ transformant, while their leucine-aminopeptidase (LAP) and endopeptidase (ENDO) activities remain unchanged. These data strongly suggested that pNFF125 contained a functional dppIV gene. In addition, when a functional gene was introduced, the DPP IV activity increased more than it should have been compared to the number of integrated copies. The difference might also come from the titration of a negatively acting transcription factor (repressor).

TABLE 1

|  | DPP IV [mU/ml] | LAP [mU/ml] | ENDO [mU/ml] |
| --- | --- | --- | --- |
| NF1 pyrG+ | 8.7 | 1.6 | 2.9 |
| Transformant 1 | 73.9 | 1.7 | 3.3 |
| Transformant 6 | 160.6 | 1.9 | 3.1 |

Characterisation of the DPP IV: culture broth from prolyl dipeptidyl peptidase overproducing transformant 6 and the control A. oryzae NF1 pyrG+ were analysed by SDS-PAGE. No single band in the prolyl dipeptidyl peptidase-overproducing strain stained more intensely than the A. oryzae NF1 pyrG+ control. However, a broad smear was visible in the region around 95 kDa of the prolyl dipeptidyl peptidase-overproducing strain, but not in the A. oryzae NF1 pyrG+ control. This aberrant electrophoretic behaviour might be caused by glycosylation of the enzyme. Therefore, culture broths were treated with N-glycosidase F and reanalysed. In the deglycosylated samples a band of 85 to 90 kDa appeared in the control NF1 pyrG+ and in the prolyl dipeptidyl peptidase overproducing transformant. A sample of the N-glycosidase F treated culture medium of transformant 6, corresponding to 100 mU prolyl dipeptidyl peptidase activity, was loaded onto a preparative gel and blotted onto an Immobilon $p^{SQ}$ membrane. The putative prolyl dipeptidyl peptidase band was excised and analysed by automated Edman degradation. The N-terminal sequence of the mature protein was determined to be Leu-Asp-Val-Pro-Arg- . . .

Sequencing of the ApaI-EcoRV fragment: the 4.8 kb fragment from pNFF125 was sequenced on both strands. The nucleotide sequence of the dppIV gene was determined, on a Licor model 4000 automatic sequencer. IRD41 labelled primer having the nucleotide sequence SEQ ID NO:3 was used for sequencing both strands of partially overlapping subclones by the dideoxynucleotide method of Sanger et al. (Proc. Natl. Acad. Sci. USA, 74, 5463–5467, 1977). The DNA sequence analysis was performed by using the GCG Computer programs (Devereux et al., Nucl. Acids Res., 12, 387–395, 1987).

The position of transcription start sites were mapped by primer extension. Additionally the position of exons and intron were determined by RT-PCR. For this purpose, total RNA was isolated from the A. oryzae TK3 mycelia cultured overnight on MMWGH, using the "RNeasy Total RNA Purification kit" (Qiagen). Reverse transcriptase PCR (RT-PCR) was performed using the "1st strand cDNA synthesis kit for RT-PCR" (Boehringer). 10 μg of total RNA, 1×reaction buffer (10 mM Tris, 50 mM KCl pH 8.3), 5 mM $MgCl_2$, 1 mM deoxynucleotide mix, 1.6 μg oligo-p(dT)$_{15}$ primer, 50 units RNAse inhibitor, 10 units AMV Reverse transcriptase were mixed and incubated 25° C. 10 min, 42° C. 60 min, 75° C. 5 min and 4° C. 5 min. 1 μl, 2 μl and 3 μl of the obtained cDNA, 2 mM of oligonucleotides and 250 mM dNTPs (Boehringer) were dissolved in 50 ml of 1×PCR buffer (20 mM Tris-HCl pH 8.55, 16 mM $(NH_4)_2SO_4$, 2.5 mM $MgCl_2$, 150 mg/ml BSA). To each reaction 1.5 unit of Taq-polymerase (Biotaq) were added as well as one drop of Nujol mineral oil (Perkin Elmer). The targeted region of the dppIV gene was amplified, using a Stratagene Robo Cycler gradient 40, with the primer pair SEQ ID NO:4 and SEQ ID NO:5. The reaction mixtures were subjected to 2 cycles of 1 min 98° C., 2 min 56° C. and 2 min 72° C., followed by 27 cycles of 1 min 94° C., 1 min 56° C. and 2 min 72° C. and 1 1 cycle of 1 min 94° C., 1 min 56° C. and 10 min 72° C. The gel purified PCR products were recovered with Qiaex II (Qiagen) and directly ligated into the pGEM-T vector (Promega) according to the instructions of the manufacturer, to generate plasmid pNFF137.

Results show that the open reading frame (ORF) is split by a 83 bp intron into 2 exons. Furthermore, the 16 aa long N-terminal secretory signal sequence was identified by homology with the A. fumigatus sequence which corresponds well to the signal sequence rule described by Von Heijne (Nucleic Acids Res., 14, 4683–4690, 1986). The dppIV gene has the nucleotide sequence SEQ ID NO:1, and encodes a mature protein of 755 aa with a deduced molecular weight of 85.4 kDa (see SEQ ID NO:2). The signal sequence of dppIV runs from position 1835 (ATG) to 1966 and includes the intron. The mature protein starts at position 1967 with the amino acid sequence LeuAspValProArg as confirmed by Edman degradation. The exon 1 starts at position 1836 and ends at position 1841; intron starts at position 1842 and ends at position 1924; exon II starts at position 1925 and ends at position 4231.

Example 2

Disruption of the dppIV Gene

In order to determine if the cloned dppIV gene was exclusively responsible for the DPP IV activity observed onto MMWGH, it was disrupted.

As heterologous selection marker, to prevent targeting of the disrupting construct to the pyrG locus, the A. nidulans pyrG gene was amplified from A. nidulans 033. To do so, the sequences between position 500 and 2342 of the pyrG gene (Oakley, et al., Gene, 61, 385–399, 1987) were amplified by PCR. 200 ng A. nidulans 033 genomic DNA, 2 mM of oligonucleotides and 250 mM dNTPs (Boehringer) were dissolved in 50 ml of 1×PCR buffer (20 mM Tris-HCl pH 8.55, 16 mM $(NH_4)_2SO_4$, 2.5 mM $MgCl_2$, 150 mg/ml BSA). To each reaction 1.5 unit of Taq-polymerase (Biotaq) were added as well as one drop of Nujol mineral oil (Perkin Elmer). The targeted region was amplified, using a Stratagene Robo Cycler gradient 40, with the primer pairs SEQ ID NO:6 and SEQ ID NO:7. The reaction mixtures were subjected to 30 cycles of 1 min 95° C., 1 min 52° C. and 3 min 72° C. The gel purified 1.8 kb PCR product was recovered with Qiaex II (Qiagen) and cloned into pGEM-T (Promega), according to the instructions of the manufacturer, to give pNFF39.

In parallel, a mutant allele of dppIV was generated from pNFF 125 by replacing the internal 1.5 kb NcoI fragment with the 1.8 kb NcoI fragment from pNFF39, creating pNFF129.

ApaI-EcoRV digested pNFF129 was introduced into A. oryzae NF1 and the transformants were grown on MM. Among 95 tested on MMWGH, eighteen transformants did not exhibit DPP IV activity. Six DPP IV negative transformants were selected and numbered from 8 to 13, and four transformants which still exhibited DPP IV activity were numbered from 14 to 17. A Southern blot of NcoI digested genomic DNA from these ten transformants was probed with the dppIV PCR fragment (see example 2). In transformants which did not exhibit DPP IV activity, the 1.5 kb NcoI fragment is absent, which proves that the wild type gene has been replaced by the disruption construct. In transformants which retain DPP IV activity, the 1.5 kb fragment is still present, and hybridising fragments with other molecular weights show that the disruption construct has integrated at another site in the genome.

To quantify DPP IV activity, transformants 10, 11 and 15 as well as A. oryzae NF1 pyrG$^+$ transformant were grown for 7 days at 30° C. on liquid MMWG. Enzymatic analyses of the supernatant (table 2) showed that transformants 10 and 11 had residual proline dipeptidyl-peptidase activity, probably due to some non specific enzymes. By contrast, transformant 15 had a higher DPP IV activity (at least 4 times more) compared to the wild type. Inspection of the original screen for DPP IV disruption mutant revealed additional clones with higher activity compared to the wild type. Since the disruption construct did not contain a functional gene, the increase of the activity might have been due to titration of a repressor.

TABLE 2

| | DPP IV [mU/ml] | LAP [mU/ml] | ENDO [mU/ml] |
| --- | --- | --- | --- |
| NF1 pyrG$^+$ | 8.7 | 1.6 | 2.9 |
| Transformant 10 | 0.4 | 5.8 | 3.1 |
| Transformant 11 | 0.1 | 6.5 | 4.5 |
| Transformant 15 | 39.6 | 5.7 | 2.7 |

Example 3
Expression of A. oryzae DPP IV in P. pastoris

Transformation of P. pastoris: plasmid pNFF125 was used as template for multiplying the dppIV gene by PCR. To do so, 200 ng of pNFF125 DNA, 164 pmol of oligonucleotides, 120 mM dNTP's were dissolved in 50 ml PCR buffer (20 mM Tris-HCl pH 8.8, 2 mM MgSO$_4$, 10 mM (NH$_4$)$_2$SO$_4$, 0.1% Triton X-100, 100 mg/ml nuclease free BSA). A drop of dynawax (Dynazyme) was added. To each reaction 2.5 unit of cloned Pfu DNA polymerase (Stratagene) was added in 50 ml of 1×PCR buffer. The A. oryzae dppIV gene was amplified with the primer pair SEQ ID NO:8 and SEQ ID NO:9 (these primers covered N- and C- terminal mature protein coding region). The reaction mixtures were subjected to thirty cycles of 1 min 95° C., 1 min 44° C. and 3 min 72° C. using Perkin Elmer DNA Thermal Cycler.

The PCR product was digested by EcoRV and NotI and cloned into the SnaBI, NotI digested pKJ115, generating the plasmid pNFF134. P. pastoris sphaeroplasts were transformed with 10 μg of pNFF134 linearised by EcoRI as described in the Manual Version 2.0. of the Pichia Expression Kit (Invitrogen).

The P. pastoris expression cassette pKJ115 can insert into the P. pastoris genome via homologous recombination at the alcohol oxidase (AOX1) site and carry, in addition to the cloned coding sequence of interest, the his4 gene for selection. Transformants were first selected on histidine-deficient media (RDB) and then screened for insertion of the construct at the aox1 site on minimal methanol plates (MMM). Transformants that were unable to grow on media containing only methanol as a carbon source (BMMY) were assumed to contain the construct in the correct yeast genomic location by integration events at the aox1 locus displacing of the aox1 coding region. The selected transformants were grown to near saturation (OD 20 at 600 nm) at 30° C. in 10 ml of glycerol-based yeast media (BMGY). Cells were harvested and resuspended in 2 ml BMMY and incubated for 2 days. After two days of incubation, the supernatant was harvested and 10 ml was analysed by SDS-PAGE according to the method of Laemmli (1970) with a separation gel of 7.5% (w/v) polyacrylamide to identify successfully expressing clones. In parallel, the supernatant was checked for activity.

Results show that the obtained concentration of DPP IV was 100 μg/ml. The activity measured in the supernatant was of about 1385 mU/ml. Among all the transformants, one was deposited under the Budapest Treaty at the Collection Nationale de Cultures de Microorganismes (CNCM), 25 rue du Docteur Roux, 75724 Paris, France, on June, where it receives the deposit number CNCM I-3.

Peptide profiling by size exclusion chromatography (SEC): the efficiency of DPP IV towards peptides in WG hydrolysates was tested. Enzymes in the supernatant of dppIV disruptant 11 thus were heat inactivated at 95° C. for 10 min. 140 mU of purified DPP IV produced by P. pastoris CNCM I-3 were added to 500 μl of supernatant and incubated at 45° C. up to 24 h. A control experiment without DPP IV addition was performed in parallel. Aliquots were taken at 2 h intervals, acidified with 10% TFA, centrifuged and analysed by SEC on a Superdex Peptide HR 10/30 column (Pharmacia Biotech, Sweden). Separation is based on molecule size of amino acids and peptides (range: 100–7'000 Da). Chromatography was performed under isocratic conditions with 0.1% TFA, 20% acetonitrile in water at a flow rate of 0.5 ml/min. Detection of amino acid and peptide peaks was at 215 nm. Peptide and amino acid standards were used to calibrate the chromatographic system (data not shown).

Results show that an initial increase of small peptides (200–500 Da) can be detected already after 2 h incubation. Extended incubation (up to 24 h) releases more dipeptides. No changes are detected in the control sample at 2 h and 24 h incubation time. Therefore, it is clear that DPP IV activity liberates dipeptides from wheat gluten hydrolysates confirming the efficiency of this enzyme in peptide degradation.

Example 4
Transformation with the Native Promoter of dppIV

The plasmid pNFF126 containing the fragment of 2094 bp ApaI-BamHI encompassing the promotor region and the start of the DPP IV gene (see SEQ ID NO:1) was introduced into A. oryzae NF1, using pyrG gene as selection marker. The A. oryzae NF1 pyrG$^+$ transformants were screened by staining for their prolyl-dipeptidyl-peptidase activity. Two transformants (B2, C7) showed a more intensive stain than the other ones. They were therefore cultured onto liquid MMWG for 7 days, 30 ° C., without shaking, in parallel with three other randomly picked transformants and the control *A. oryzae* NF1 transformed with only pyrG.

The prolyl-dipeptidyl-peptidase activity was analysed from the culture broths. Results show that transformants B2 and C7 respectively showed a fourfold and twofold increase of the prolyl dipeptidyl peptidase activity compared to the control, whereas all the other ones do not exhibit any increase of this activity. In the disruption experiment (see example 2), also a maximum of fourfold increase of the prolyl-dipeptidyl-peptidase activity was noticed (transformant 15). This increase can be due to a repressor titrated by the multicopies of the promotor region integrated heterologously in the genome of *A. oryzae* NF1 or by a positive acting factor encoded by the 2094 bp ApaI-BamHI fragment.

Example 5
Functional Derivatives of the DPP IV

Functional derivatives of the DPP IV (SEQ ID NO:2) are prepared according to a method adapted from the method described by Adams et al. (EP402450; Genencor). Briefly, the expression cassette pKJ115 containing the DPP IV was subjected to an in-vitro chemical mutagenesis by hydroxylamine. According to example 3, the mutagenised DNA was then used to transform *P. pastoris*. Functional derivatives of the DPP IV, presenting a deletion, addition and/or a substitution of some amino acids, were finally detected according to their peptide profile obtained by hydrolysing wheat gluten with purified DPP IV derivatives (see example 3).

Examples 6

For preparing a fermented soya sauce, a koji is prepared by mixing an *Aspergillus oryzae* CNCM I-1 koji culture with a mixture of cooked soya and roasted wheat, the koji is then hydrolysed in aqueous suspension for 3 to 8 hours at 45° C. to 60° C. with the enzymes produced during fermentation of the *Aspergillus oryzae* CNCM I-1 culture, a moromi is further prepared by adding suitable amount of sodium chloride to the hydrolysed koji suspension, the moromi is left to ferment and is then pressed and the liquor obtained is pasteurized and clarified.

Examples 7

For producing a flavouring agent, a aqueous suspension of a mixture of cooked soya and roasted wheat is prepared, the proteins are solubilized by hydrolysis of the suspension with a protease at pH 6.0 to 11.0, the suspension is heat-treated at pH 4.6 to 6.5, and the suspension is ripened with enzymes of a koji culture fermented by *Aspergillus oryzae* CNCM I-2.

What is claimed is:

1. A recombinant prolyl-dipeptidyl-peptidase (DPP IV) from *Aspergillus oryzae* comprising the amino-acid sequence from amino acid 1 to amino acid 755 of SEQ ID NO:2 or polypeptides having at least 80% identity to amino acids 1–755 of SEQ ID NO:2 having prolyl-dipeptidyl peptidase activity.

2. A recombinant prolyl-dipeptidyl-peptidase according to claim 1 which is fused to a leader peptide.

3. A recombinant prolyl-dipeptidyl-peptidase according to claim 2 which is fused to the leader peptide of *Aspergillus oryzae* DDP IV having the amino-acid sequence from amino acid-16 to amino acid-1 of SEQ ID NO:2 or variants thereof having at least 80% identity to amino acids −16 to −1 of SEQ ID NO:2, wherein said variants are able to integrate the DPP IV into the cell wall or the cell membrane or secrete the enzyme into the periplasmic space or into the culture medium.

4. A leader peptide of *Aspergillus oryzae* DPP IV having the amino-acid sequence from amino acid-16 to amino acid-1 of SEQ ID NO:2 or variants thereof having at least 80% identity to amino acids −16 to −1 of SEQ ID NO:2, wherein said variants are able to integrate the DPP IV into the cell wall or the cell membrane or secrete the enzyme into the periplasmic space or into the culture medium.

5. An isolated DNA molecule which comprises a dppIV gene encoding DPP IV according to claim 1.

6. An isolated DNA molecule according to claim 5, which is a vector comprising the dppIV gene.

7. An isolated DNA molecule according to claim 5, wherein the dppIV gene is operably linked to at least one regulatory sequence able to direct the expression of the gene.

8. A DNA molecule according to claim 7, wherein the regulatory sequence is derived from another organism than the one from which the dppIV gene is derived.

9. An isolated DNA molecule according to claim 5, wherein dppIV gene comprises the coding parts of the nucleotide sequence SEQ ID NO:1 or variants thereof encoding polypeptides having at least 80% identify to amino acids 1–755 of SEQ ID NO:2 having prolyl-dipeptidyl peptidase activity.

10. A cell which expresses DPP IV according to claim 1 by recombinant technology.

11. A cell according to claim 10, which is *Pichia pastoris* CNCM I-1886.

12. A cell according to claim 10 which is able to over-express DPP IV.

13. A cell according to claim 12, which is *Aspergillus oryzae* capable of providing at least 50 mU of prolyl-dipeptidyl-peptidase activity per ml of supernatant when grown in a minimal medium containing 1% (w/v) of wheat gluten.

14. An *Aspergillus oryzae* which is able to over-express the enzyme according to claim 1 by recombinant technology wherein multiple recombinant functional dppIV genes have been integrated.

15. An *Aspergillus oryzae* according to claim 14 which is the *Aspergillus oryzae* CNCM I-1888.

16. An Aspergillus which has integrated multiple copies of the promoter having the coding nucleotide sequence from nucleotide 1836 to nucleotide 1966 of SEQ ID NO:1.

17. An *Aspergillus oryzae* according to claim 16, which is the *Aspergillus oryzae* CNCM I-1887.

18. An Aspergillus naturally providing a prolyl-dipeptidyl-peptidase activity which is manipulated genetically so that dppIV gene is inactivated.

19. A method for producing a recombinant prolyl-dipeptidyl-peptidase (DPP IV) from *Aspergillus oryzae* comprising the amino-acid sequence from amino acid 1 to amino acid 755 of SEQ ID NO:2 or polypeptides having at least 80% identity to amino acids 1–755 of SEQ ID NO:2 having prolyl-dipeptidyl peptidase activity comprising cultivating recombinant cells according to claim 10 in a suitable growth medium under conditions that the cells express the enzyme, and optionally isolating the enzyme in the form of a concentrate.

\* \* \* \* \*

UNITED STATES PATENT AND TRADEMARK OFFICE
CERTIFICATE OF CORRECTION

PATENT NO.   : 6,309,868 B1
DATED        : October 30, 2001
INVENTOR(S)  : Monod et al.

It is certified that error appears in the above-identified patent and that said Letters Patent is hereby corrected as shown below:

<u>Title page,</u>
Item [75], Inventors, change the city of residence of the second-named inventor from "Gollian" to -- Gollion --; and change the city of residence of the fourth-named inventor from "Ch-Epalinges" to -- Epalinges --.

Item [56], OTHER PUBLICATIONS,
change "(1988)" to -- (1998) --.

<u>Column 25,</u>
Line 64, change "DDP" to -- DPP --.

<u>Column 27,</u>
Line 1, change "A DNA" to -- An isolated DNA --.
Line 7, change "identify" to -- identity --.

Signed and Sealed this

Nineteenth Day of March, 2002

Attest:

*Attesting Officer*

JAMES E. ROGAN
*Director of the United States Patent and Trademark Office*

SEQUENCE LISTING

```
<160> NUMBER OF SEQ ID NOS:  9

<210> SEQ ID NO 1
<211> LENGTH: 5496
<212> TYPE: DNA
<213> ORGANISM: Fungus

<400> SEQUENCE: 1
gggccctgag tttaacggtg ctgggtgtgt tattacgcat catactcttc acccgccttg     60
cagtagttcg gttctattgt caatagctgc tgtcgcaata ttctgtcttt tgccaataag    120
gtgaccagga ggggtctttc caggatagat agatggcgac atttatctcg tcgcggcggt    180
gattgtctgt ttgattgatg atgatctctg aaacatgttg aatctggggt acgtaacttg    240
gggtgatcaa ttgacatcca cttagatatg gtacagcaaa gtataccycc tggattctgt    300
gaacaagaat ataaaataag cctcgcgacc gggagtcttg tccctcaaat catcacaatc    360
ccatcgaaca tccgcatcta atttcctcac tcatccttct atccaccgcc aaaatgaagg    420
ccgctaccct cctctctctt ctgagcgtta ccggactcgt cgccgctgct ccagctggca    480
acggtacgta tcctgaacga caatgtaaga cgcttgactg atgattagta ggcccagctg    540
gtggaatcat cgaccgcgat cttcccgtcc ctgtccctgg actccctacc aagggtctcc    600
ctattgttga cggattgact ggcggcaata agggtggcga gaagcctgga agcaaggtta    660
ctcctcgtga agaccctacc ggcagcgccc ctgatggcaa gggcaatgat ggccccgacg    720
gtgatcttac cggacgtccc ggtcaagggg gtcttgacaa ccctttcgat ctccctactc    780
cagagcttcc tcccgtcaag cttcctggcg gacttgacgg tggcaagggc ggtctcggcc    840
ttcgtcgtcg tggcagccca gtagacggtc tccctgtcgt tgggcctgtt gttggtggtg    900
ttctaggtgg cggtggtgct ggcagtggtg ctggtgccaa gggtggtgct ggtagtggta    960
ccgttgggcg tcgtggcagc ccagtagacg gtctccctgt tgttgggcct gttgttggtg   1020
```

-continued

```
gtgtcctagg tggcggtggt gctggcagtg gtgctggtgc aagggtggt gctggtagtg      1080
gtacccctaa gcgccgtgac ggtccagtgg acggtgttcc tgtcgttgga gagcttgctg      1140
aaggtgctac tggaggtctt ctaggtggtg atgctggttc tgctgatgct gctggtgctg      1200
atgctggtgc tgatgctggt gctggtgctg gtgggcaata gtctaacaag ggctttacgg      1260
catcaatgtg aggttatcca acatccatcc ttggtggcca ttcgtaaata gcaacaaaga      1320
ggggtggtac ttggtcgcga tgtcattgct cctgcgattg aagctagcga ttcctgtatg      1380
tacaataatt ttaagcacgc ttggttccat actgtttctt cactggtttt tggatatttt      1440
ttcacttatt gaatcttgta gtagtccagc ttctcatggt tagacacggg ataacccccc      1500
aatagcatca tctgcaggtt tgatgttgca atggtcaagt tttgtcttaa attatgtacg      1560
agtcttgggt taccccgcta aagctttgc caccaatgaa gctgttgctt gtccaacggc      1620
tatcagcggt tttttttatg agaatcttgg caggatagga aaagttggtg gtggtgaagg      1680
agctaatgca ggaggtggag tgactgataa gacgcgattt ctgcggggaa aaagaaaaag      1740
gaccaattta tgggactatt tatttaaacg ggaagtcttc aattccgttc gccagccatc      1800
ccttgattcg agctgaactc ggggtttttt ccaccatgaa ggtacgtcaa ttccactgat      1860
taaacattat ttgttacata cactccatca ttgagtcaat tataattaac acctcataat      1920
tcagtactcc aagcttctgc tgctcctggt cagtgtggtc caggccctgg atgtgcctcg      1980
gaaaccacac gcgccaccg gagaaggcag taagcgtctc accttcaatg agaccgtagt      2040
caagcaagca attacgccga cctctcgctc ggtgcaatgg ctctcgggcg cagaggatgg      2100
atccctacgt gtacgcggcg gaagacggca gtctcaccat cgagaacatc gtcaccaacg      2160
agtcacgcac gctcatcctg cggacaagat tccgacaggg aaggaagcgt tcaattactg      2220
gatccatccc gacttgtcgt cggtgctgtg ggcgtccaac cacaccaagc agtatcggca      2280
ttcgttcttt gccgattatt acgtccagga tgtggagtca ctcaagtccg tgcccctgat      2340
gcccgatcag gaaggtgata ttcaatatgc ccaatggagc cccgtgggca ataccatcgc      2400
ttttgttcgc gagaatgacc tttatgtctg ggataatggt accgttactc gcattactga      2460
tgatggtggc cccgacatgt tccacggcgt gccggactgg atctatgaag aggagatcct      2520
cggcgatcgc tacgcgttgt ggttctcgcc agatggtgaa tatctggctt acttgagctt      2580
caatgagact ggggttccga cctacaccgt tcagtattat atggataacc aagagatcgc      2640
tccggcgtat ccatgggagc tgaagataag gtatcccaag gtgtcgcaga cgaatccgac      2700
cgtgacgttg agtctgctta acatcgctag caaggaggtg aagcaggcgc cgatcgacgc      2760
gttcgagtca actgacttga tcattggcga ggttgcttgg ctcactgata ctcacaccac      2820
cgttgctgct aaggcgttca accgtgtcca ggaccagcaa aaggtcgtcg cggtcgatac      2880
tgcctcgaac aaggctactg tcatcagcga ccgagatggg accgatggat ggctcgataa      2940
ccttctttca atgaagtata ttggccctat caagccgtcc gacaaggatg cctactacat      3000
cgacatctct gaccattcgg gatgggcgca tctgtatctc ttccccgttt cgggcggcga      3060
acctatccca ctaaccaaag gcgactggga ggtcacgtct attctgagta ttgatcagga      3120
acgccagttg gtgtactacc tgtcgactca acaccacagc accgagcgcc atctctactc      3180
cgtctcctat tccacgtttg cggtcacccc gctcgtcgac gacaccgttg ccgcgtactg      3240
gtctgcttcc ttctccgcga actcgggcta ctacatcctc acatacggag cccagacgt      3300
accctaccag gaactctaca cgaccaacag taccaaacca ctccgcacaa tcaccgacaa      3360
cgccaaagta ctcgagcaaa tcaaggacta tgcattgccc aacatcacct acttcgagct      3420
```

```
tcccctcccc tccggagaaa ccctcaatgt gatgcagcgc ttaccccccg ggttctcccc    3480
ggataagaag tacccatac ttttcacccc atacggcggc ccaggcgccc aagaagtgac    3540
caagagatgg caagccctga atttcaaggc ctatgtcgcc tccgacagcg aactcgagta    3600
cgtaacctgg actgtcgaca accgcggcac aggtttcaaa ggacgcaagt tccgctccgc    3660
cgtcacgcgc caactcggcc cctcgaagc agaagaccag atctacgccg cgcaacaggc    3720
ggccaacatc ccctggatcg atgcagacca catcggcatc tggggctgga gtttcggagg    3780
ctacttgacc agcaaggtcc tggagaagga cagcggtgct ttcacattag gagtcatcac    3840
cgcccctgtt tctgactggc gtttctacga ctcaatgtac acggagcgct acatgaagac    3900
cctctcgacc aatgaggagg ctacgagac cagcgccgtc cgcaagactg acgggttcaa    3960
gaacgtcgag ggcggattct tgatccagca cggaacgggc gacgataacg tccatttcca    4020
gaactcggct gcgctggtgg atctcctgat gggcgatgcg gtctctcctg agaagctcca    4080
ttcgcaatgg ttcacagact cagaccacgg aatcagctac catggtggcg gcgtgttcct    4140
gtacaagcaa ctggcccgga agctctacca ggagaagaac cgacgacgc aggtgctgat    4200 gcaccagtgg actaagaagg acttggagga gtagaagcgg cacatcattc attcatttta    4260
aagcgactgg ctacacatag catacatagc aattgatact tcgtatttta ccctccccac    4320
agccacgacc atcacccatt ggcgcaaaat tctccccgca ccataaacta gcgcgacgag    4380
gctgaaaatc tgccagaaat ctacttaaag ctcgtgttgg cccagtccct cacaacccaa    4440
accatcccaa gtaaacaaaa ccaaaaaaaa atcccataga aaatggccga catccccacc    4500
tcaacagtcc aaatcacaac cctcccccacc aaatccgtaa caatcacccc gcaacgagcg    4560
accatcgttc gcgagataca cacctccatc caggtatgca cataccacct cacctgacca    4620
tccaacccta cttacagtca acgtaaacta acaaaattaa aaaaataaaa agacaggcca    4680
acacgaacta ataatcaccg gcctcgaccc aagagtagac accgactcca ttttactcga    4740
aggaacagga acggccacaa taaccgatat ccaaacctcg atagtccccc gacaggaaaa    4800
attcgaggat atctatcccg ccgaatcaga ctccgacgac tccccagagc ccgattccga    4860
ctccgacctt gaccacgatg accccgagtt acaagctatc tccgcatcca tagccgaagt    4920
cgaagcgcga cttgcgcgag cggaaaatga acagacgatg gcggtttcca tccgggagtt    4980
tctggatggg tatgccaaga agatggatcc ggagcatgtg gacgcggaga tgctagatgg    5040
gttcttgggg ctttatacccc ggcagcgggt ggagggtttt cagcggcatc atcaggctgg    5100
ggtggagtat gggaagggg gagagggagct tgcgcggttg gtgaagagga acgcgggaag    5160
attgagggtc ggttgaagag ggctagggag gtggtgaaga agaaggagcg gagggagagg    5220
gagaagagag ccaccgagcg tgcgaggaag actgaacagc ggaagatgaa gagggaggag    5280
agactcaagt tctggacgac gcgggttggg caggtggttg tgtcatctgg atagtcaggc    5340
cgggactwgc cggcgcagtt ccatcgttga atcgggttga acggttktct ggttgtgtgt    5400
agtatttcat gcggagcctg tgtggatgtc gacgtgtgcg tgctgagact atgttgtgta    5460
cgwmtataga tttaattaag gatcckgcgt gccgcc                            5496
```

<210> SEQ ID NO 2
<211> LENGTH: 771
<212> TYPE: PRT
<213> ORGANISM: Fungus

<400> SEQUENCE: 2

-continued

```
Met Lys Tyr Ser Lys Leu Leu Leu Leu Val Ser Val Val Gln Ala
 1               5                  10                  15

Leu Asp Val Pro Arg Lys Pro His Ala Pro Thr Gly Glu Gly Ser Lys
            20                  25                  30

Arg Leu Thr Phe Asn Glu Thr Val Lys Gln Ala Ile Thr Pro Thr
            35                  40                  45

Ser Arg Ser Val Gln Trp Leu Ser Gly Ala Glu Asp Gly Ser Leu Arg
    50                  55                  60

Val Arg Gly Gly Arg Arg Gln Ser His His Arg Glu His Arg His Gln
65                  70                  75                  80

Arg Val Thr His Ala His Pro Ala Asp Lys Ile Pro Thr Gly Lys Glu
                85                  90                  95

Ala Phe Asn Tyr Trp Ile His Pro Asp Leu Ser Ser Val Leu Trp Ala
                100                 105                 110

Ser Asn His Thr Lys Gln Tyr Arg His Ser Phe Phe Ala Asp Tyr Tyr
            115                 120                 125

Val Gln Asp Val Glu Ser Leu Lys Ser Val Pro Leu Met Pro Asp Gln
    130                 135                 140

Glu Gly Asp Ile Gln Tyr Ala Gln Trp Ser Pro Val Gly Asn Thr Ile
145                 150                 155                 160

Ala Phe Val Arg Glu Asn Asp Leu Tyr Val Trp Asp Asn Gly Thr Val
                165                 170                 175

Thr Arg Ile Thr Asp Asp Gly Gly Pro Asp Met Phe His Gly Val Pro
                180                 185                 190

Asp Trp Ile Tyr Glu Glu Glu Ile Leu Gly Asp Arg Tyr Ala Leu Trp
            195                 200                 205

Phe Ser Pro Asp Gly Glu Tyr Leu Ala Tyr Leu Ser Phe Asn Glu Thr
    210                 215                 220

Gly Val Pro Thr Tyr Thr Val Gln Tyr Tyr Met Asp Asn Gln Glu Ile
225                 230                 235                 240

Ala Pro Ala Tyr Pro Trp Glu Leu Lys Ile Arg Tyr Pro Lys Val Ser
                245                 250                 255

Gln Thr Asn Pro Thr Val Thr Leu Ser Leu Leu Asn Ile Ala Ser Lys
            260                 265                 270

Glu Val Lys Gln Ala Pro Ile Asp Ala Phe Glu Ser Thr Asp Leu Ile
    275                 280                 285

Ile Gly Glu Val Ala Trp Leu Thr Asp Thr His Thr Thr Val Ala Ala
290                 295                 300

Lys Ala Phe Asn Arg Val Gln Asp Gln Gln Lys Val Val Ala Val Asp
305                 310                 315                 320

Thr Ala Ser Asn Lys Ala Thr Val Ile Ser Asp Arg Asp Gly Thr Asp
                325                 330                 335

Gly Trp Leu Asp Asn Leu Leu Ser Met Lys Tyr Ile Gly Pro Ile Lys
            340                 345                 350

Pro Ser Asp Lys Asp Ala Tyr Tyr Ile Asp Ile Ser Asp His Ser Gly
    355                 360                 365

Trp Ala His Leu Tyr Leu Phe Pro Val Ser Gly Gly Glu Pro Ile Pro
    370                 375                 380

Leu Thr Lys Gly Asp Trp Glu Val Thr Ser Ile Leu Ser Ile Asp Gln
385                 390                 395                 400

Glu Arg Gln Leu Val Tyr Tyr Leu Ser Thr Gln His His Ser Thr Glu
                405                 410                 415

Arg His Leu Tyr Ser Val Ser Tyr Ser Thr Phe Ala Val Thr Pro Leu
```

```
                        420                 425                 430
Val Asp Asp Thr Val Ala Ala Tyr Trp Ser Ala Ser Phe Ser Ala Asn
                435                 440                 445
Ser Gly Tyr Tyr Ile Leu Thr Tyr Gly Gly Pro Asp Val Pro Tyr Gln
        450                 455                 460
Glu Leu Tyr Thr Thr Asn Ser Thr Lys Pro Leu Arg Thr Ile Thr Asp
465                 470                 475                 480
Asn Ala Lys Val Leu Glu Gln Ile Lys Asp Tyr Ala Leu Pro Asn Ile
                485                 490                 495
Thr Tyr Phe Glu Leu Pro Leu Pro Ser Gly Thr Leu Asn Val Met
                500                 505                 510
Gln Arg Leu Pro Pro Gly Phe Ser Pro Asp Lys Lys Tyr Pro Ile Leu
        515                 520                 525
Phe Thr Pro Tyr Gly Gly Pro Gly Ala Gln Glu Val Thr Lys Arg Trp
        530                 535                 540
Gln Ala Leu Asn Phe Lys Ala Tyr Val Ala Ser Asp Ser Glu Leu Glu
545                 550                 555                 560
Tyr Val Thr Trp Thr Val Asp Asn Arg Gly Thr Gly Phe Lys Gly Arg
                565                 570                 575
Lys Phe Arg Ser Ala Val Thr Arg Gln Leu Gly Leu Leu Glu Ala Glu
                580                 585                 590
Asp Gln Ile Tyr Ala Ala Gln Gln Ala Ala Asn Ile Pro Trp Ile Asp
                595                 600                 605
Ala Asp His Ile Gly Ile Trp Gly Trp Ser Phe Gly Gly Tyr Leu Thr
        610                 615                 620
Ser Lys Val Leu Glu Lys Asp Ser Gly Ala Phe Thr Leu Gly Val Ile
625                 630                 635                 640
Thr Ala Pro Val Ser Asp Trp Arg Phe Tyr Asp Ser Met Tyr Thr Glu
                645                 650                 655
Arg Tyr Met Lys Thr Leu Ser Thr Asn Glu Glu Gly Tyr Glu Thr Ser
                660                 665                 670
Ala Val Arg Lys Thr Asp Gly Phe Lys Asn Val Glu Gly Gly Phe Leu
                675                 680                 685
Ile Gln His Gly Thr Gly Asp Asp Asn Val His Phe Gln Asn Ser Ala
        690                 695                 700
Ala Leu Val Asp Leu Leu Met Gly Asp Gly Val Ser Pro Glu Lys Leu
705                 710                 715                 720
His Ser Gln Trp Phe Thr Asp Ser Asp His Gly Ile Ser Tyr His Gly
                725                 730                 735
Gly Gly Val Phe Leu Tyr Lys Gln Leu Ala Arg Lys Leu Tyr Gln Glu
                740                 745                 750
Lys Asn Arg Gln Thr Gln Val Leu Met His Gln Trp Thr Lys Lys Asp
                755                 760                 765
Leu Glu Glu
        770

<210> SEQ ID NO 3
<211> LENGTH: 18
<212> TYPE: DNA
<213> ORGANISM: Fungus

<400> SEQUENCE: 3
gcctggacca cactgacc                                              18
```

-continued

```
<210> SEQ ID NO 4
<211> LENGTH: 18
<212> TYPE: DNA
<213> ORGANISM: Fungus

<400> SEQUENCE: 4
tccaccatga agtactcc                                                   18

<210> SEQ ID NO 5
<211> LENGTH: 18
<212> TYPE: DNA
<213> ORGANISM: Fungus

<400> SEQUENCE: 5
atcgccgagg atctcctc                                                   18

<210> SEQ ID NO 6
<211> LENGTH: 23
<212> TYPE: DNA
<213> ORGANISM: Fungus

<400> SEQUENCE: 6
gaattccatg gtgtcctcgt cgg                                             23

<210> SEQ ID NO 7
<211> LENGTH: 24
<212> TYPE: DNA
<213> ORGANISM: Fungus

<400> SEQUENCE: 7
gaattcgagc cgtcagtgag gctc                                            24

<210> SEQ ID NO 8
<211> LENGTH: 32
<212> TYPE: DNA
<213> ORGANISM: Fungus

<400> SEQUENCE: 8
tggtcgatat cctggatgtg cctcggaaac ca                                   32

<210> SEQ ID NO 9
<211> LENGTH: 30
<212> TYPE: DNA
<213> ORGANISM: Fungus

<400> SEQUENCE: 9
ttgcggccgc tactcctcca agtccttctt                                      30
```